(12) United States Patent
Choi

(10) Patent No.: US 6,657,073 B1
(45) Date of Patent: Dec. 2, 2003

(54) CRYSTALLIZATION OF α-L-ASPARTYL-L-PHENYLALANINE METHYL ESTER

(75) Inventor: Cheong-Song Choi, Seoul (KR)

(73) Assignee: Daesang Corporation, Kyungki-do (KR)

(*) Notice: Subject to any disclaimer, the term of this patent is extended or adjusted under 35 U.S.C. 154(b) by 0 days.

(21) Appl. No.: 09/653,662

(22) Filed: Sep. 1, 2000

Related U.S. Application Data

(63) Continuation-in-part of application No. 09/641,988, filed on Aug. 18, 2000.
(60) Provisional application No. 60/149,570, filed on Aug. 18, 1999.

(51) Int. Cl.$^7$ .............................................. C07C 229/00
(52) U.S. Cl. ........................................... 560/40; 560/41
(58) Field of Search .............................. 117/11; 560/41, 560/40

(56) References Cited

U.S. PATENT DOCUMENTS

| | | |
|---|---|---|
| 4,150,952 A | 4/1979 | Lafleur et al. |
| 4,606,854 A | 8/1986 | Ozawa et al. |
| 4,710,231 A | 12/1987 | Bateman et al. |

(List continued on next page.)

FOREIGN PATENT DOCUMENTS

| | | |
|---|---|---|
| DE | 199 12 699 A1 | 9/2000 |
| DE | 19912699 A1 | 9/2000 |
| EP | 0 399 605 A1 | 11/1990 |
| EP | 0 405 273 A2 | 1/1991 |
| EP | 0 484 769 A2 | 10/1991 |
| EP | 0 484 769 A2 | 5/1992 |
| EP | 0 547 342 A1 | 10/1992 |
| EP | 0733 641 A1 | 9/1996 |
| EP | 0 976 762 A1 | 2/2000 |
| EP | 1 077 216 A1 | 2/2001 |

OTHER PUBLICATIONS

Kishimoto, et al., *The 'bundling' phenomenon in aspartame crystallisation*, Chem. Inc 16 (1987).
Kishimoto, et al., *A Process Development for the Bundling Crystallization of Aspartame*, J. Chem. Tech. Biotechnol. 43:71–82 (1988).
Kishishita, et al., *Characterization of organic crystal products*, J. Crystal Growth 167:729–733 (1996).
Kishishita, et al., *The Bundle–like Crystals of Aspartame in Static Crystallization*, International Symposium on Industrial Crystallization pp. 635–646 Sep. 17–18, 1998.
Kishishita, et al., *Characterization of Aspartame Crystals*, Ind. Eng. Chem. Res. 38:2166–2170 (1999).
Leung, et al., *Solid State Stability of Model Dipeptides: Aspartame and Aspartylphenylalanine*, J. Pharm. Sci. 86(1):64–71 (1997).
Leung, et al., *Solid–State Characterization of Two Polymorphs of Aspartame Hemihydrate*, J. Pharm, Sci. 87(4):501–507 (1998).
Leung, et al., *Hydration and Dehydration Behavior of Aspartame Hemihydrate*, J. Pharm. Sci. 87(4):508–513 (1998).

(List continued on next page.)

*Primary Examiner*—Johann Richter
*Assistant Examiner*—Paul A. Zucker
(74) *Attorney, Agent, or Firm*—Knobbe, Martens, Olson & Bear, LLP

(57) ABSTRACT

The present invention provides a novel process for the crystallization of α-L-aspartyl-L-phenylalanine methyl ester crystals wherein initial nucleation and initial crystal growth is conducted in a controlled manner in a metastable supersaturated solution, followed by further crystal growth via a cooling crystallization step. The process disclosed herein can be performed in an industrial scale.

72 Claims, 4 Drawing Sheets

U.S. PATENT DOCUMENTS

| | | |
|---|---|---|
| 4,803,300 A | 2/1989 | Hijiya et al. |
| 4,820,861 A | 4/1989 | Yukawa et al. |
| 4,908,472 A | 3/1990 | Takaki et al. |
| 4,994,605 A | 2/1991 | Kishimoto et al. |
| 5,041,607 A | 8/1991 | Naruse et al. |
| 5,097,060 A | 3/1992 | Naruse et al. |
| 5,202,235 A | 4/1993 | Iacobucci |
| 5,266,719 A | 11/1993 | Kishimoto et al. |
| 5,286,897 A | 2/1994 | Kurauchi et al. |
| 5,298,648 A | 3/1994 | Ebisawa et al. |
| 5,312,977 A | 5/1994 | Yanaka et al. |
| 5,371,269 A | 12/1994 | Nagashima et al. |
| 5,391,810 A | 2/1995 | Abe et al. |
| 5,425,787 A | 6/1995 | Abe et al. |
| 5,501,712 A | 3/1996 | Abe et al. |
| 5,530,106 A | 6/1996 | Navia et al. |
| 5,532,015 A | 7/1996 | Hirano et al. |
| 5,532,407 A | 7/1996 | Takemoto et al. |
| 5,581,009 A | 12/1996 | Hijiya et al. |
| 5,591,886 A * | 1/1997 | Ichiki et al. |
| 5,621,137 A | 4/1997 | Naruse et al. |
| 5,659,066 A * | 8/1997 | Murakami et al. |
| 5,733,883 A | 3/1998 | Rijkers et al. |
| 5,744,632 A | 4/1998 | Naruse et al. |
| 5,859,282 A | 1/1999 | Naruse et al. |
| 5,874,609 A | 2/1999 | Naruse et al. |
| 6,179,912 B1 | 1/2001 | Barbera-Guillem et al. |
| 6,315,966 B1 | 11/2001 | Baumgard et al. |

OTHER PUBLICATIONS

Mori, et al., *Spherulitic crystallization of aspartame from aqueous solution in a two–dimensional cell, J. Crystal Growth* 133:80–86 (1993).

Declaration of Dr. Shin' ichi Kishimoto dated Apr. 2, 2001.

Declaration of Masayoshi Naruse dated Apr. 3, 2001.

Mori, et al., "Spherulitic crystallization of aspartame from aqueous solution in a two–dimensional cell," *Journal of Crystal Growth*, 133:80–86 (1993).

Kishimoto, "A Process Development for the Bundling Crystallization of Aspartame," *J. Chem. Tech. Biotechnol.*, 43:71–82 (1988).

Levene, Journal of Biological Chemistry, Preparation of I–Mannose, 1923, 57, pp. 329–336.*

* cited by examiner

CRYSTALLIZATION OF α-L-ASPARTYL-L-PHENYLALANINE METHYL ESTER

RELATED APPLICATION

This application is a continuation-in-part, of U.S. patent application Ser. No. 09/641,988, filed Aug. 18, 2000, now pending, which claims the benefit of earlier filing date of U.S. Provisional Application No. 60/149,570 filed Aug. 18, 1999.

BACKGROUND OF THE INVENTION

1. Field of the Invention

The present invention relates to a method for producing α-L-aspartyl-L-phenylalanine methyl ester ("α-APM" or "aspartame"). More particularly, this invention pertains to the crystallization of α-APM from a metastable supersaturated solution.

2. Description of the Related Art

Aspartame or α-APM is a well-known low calorie sweetener that is widely used in a variety of food and beverage products. Various methods for crystallizing α-APM have been proposed, including cooling crystallization.

A typical cooling crystallization process begins with a hot unsaturated feed solution being charged to a reactor equipped with a heat exchanger for cooling. A supersaturated state is created shortly after cooling begins. Nucleation then occurs, crystals grow, and supersaturation is depleted. Because the crystal size distribution is dependent on the supersaturation profile of the crystallization process as it occurs, the cooling rate is of critical importance in determining the resulting crystal size distribution. Therefore, the cooling rate must be closely monitored and controlled in order to achieve optimal crystal size distribution.

However, such control can be difficult to achieve when the crystallization method utilizes an agitated crystallizer equipped with a cooling jacket or coil. In such a system, crystals are deposited on the cooling surface of the crystallizer. This has the effect of drastically reducing the heat transfer coefficient between the surface and solution, thereby reducing the efficiency of the cooling process and making it more difficult to control the cooling rate, and thus the crystal size distribution. Moreover, the crystals produced by such a method often display poor filterability, which makes further processing of the precipitated crystals difficult.

Another process known in the art for preparing α-APM crystals comprises cooling an aqueous solution of α-APM through conduction heat transfer without mechanical agitation. Such a method produces a sherbet-like pseudo-solid phase of α-APM crystals. The crystals produced by such a method demonstrate better filterability than those produced by the conventional cooling process described above wherein the mixture is stirred during crystallization. However, a crystallization method involving cooling through heat transfer without mechanical agitation has the disadvantage of requiring a very long operation time.

SUMMARY OF THE INVENTION

Accordingly, in a first embodiment of the present invention, a method of producing crystals of α-L-aspartyl-L-phenylalanine methyl ester ("α-APM") is provided, the method including the steps of forming a supersaturated solution of α-APM, initiating nucleation of α-APM crystal nuclei to form a suspension of crystal nuclei in the supersaturated solution, and growing the α-APM crystal nuclei in the supersaturated solution to form the crystals without substantial formation of new crystal nuclei.

In aspects of this embodiment, the step of forming the supersaturated solution includes preparing a non-saturated α-APM solution and cooling the non-saturated solution to form the supersaturated solution. The concentration of the non-saturated α-APM solution may preferably be in the range from about 1.5 wt. % to about 7.0 wt. %, and more preferably from about 3.0 wt. % to about 5.5 wt. %. The temperature of the non-supersaturated α-APM solution may preferably be in the range from about 35° C. to about 85° C. before cooling, more preferably from about 55° C. to about 75° C. before cooling. The cooling step may be conducted at less than a maximum allowable undercooling at a concentration, or by heat exchanging with a coolant. The solution may be an aqueous solution, and the concentration of α-APM in the supersaturated aqueous solution prior to initiating nucleation may be greater than about 3.5 wt. %. The step of initiating nucleation may be conducted by mechanical forcing of the solution, such as by a pump, preferably a peristaltic pump. The step of initiating nucleation may also be conducted by introducing seed crystals into the solution. The step of initiating nucleation may be conducted at a solution temperature ranging from about 28° C. to about 80° C., more preferably from about 48° to about 66° C.

In further aspects of this embodiment, the step of growing the α-APM crystal nuclei may include a spontaneous growing stage after the initiation of nucleation and a forced growing stage after the spontaneous growing stage. The spontaneous growing stage may proceed at a supersaturated solution temperature ranging from about 45° C. to 60° C. The forced growing stage may include cooling the suspension of crystal nuclei in the supersaturated solution. The cooling may be conducted at a temperature ranging from about 5° C. to 60° C., in a batch or continuous mode operation, or for a time of from about 50 to about 500 min. The suspension of crystal nuclei in the supersaturated solution may be stirred during the cooling, such as by an anchor type impeller or a ribbon type impeller, and a scraper may be attached to the impeller. The stirring may be conducted at from about 2 rpm to about 100 rpm. The suspension of crystal nuclei in the supersaturated solution should not be in contact with a gaseous atmosphere before the cooling.

In yet other aspects of this embodiment, the method further includes conducting a solid-liquid separation after growing the α-APM crystal nuclei in the supersaturated solution to form α-APM crystals. The α-APM crystals may then be dried under elevated temperature.

In a second embodiment of the present invention, a method of continuously crystallizing a solute dissolved in a solution is provided, the method including continuously feeding a supersaturated solution to a peristaltic pump, continuously generating crystal nuclei of a solute in the supersaturated solution by rolling action of the pump to form a suspension of crystal nuclei in the supersaturated solution, continuously transferring the suspension to a crystallizer, and continuously growing the crystal nuclei by cooling the suspension in the crystallizer without substantial formation of new nuclei.

In aspects of this embodiment, the step of continuously feeding may include continuously cooling a non-saturated solution to form a supersaturated solution. The step of continuously growing may include continuously stirring the suspension or continuously scraping an internal surface of the crystallizer. The stirring may be provided by an anchor type impeller or a ribbon type impeller. The method may further include continuously withdrawing the suspension from the crystallizer.

In a third embodiment of the present invention, an apparatus for use in crystallization of a solute dissolved in a solvent is provided, the apparatus including a source of a supersaturated solution of a solute, a peristaltic pump in fluid communication with the supersaturated solution, and a crystallizer in fluid communication with the pump.

In aspects of this embodiment, the apparatus may further include a transfer line, optionally equipped with a heat exchanger, in fluid communication with the source and the pump. The crystallizer, optionally equipped with a heat exchanger, may include a cooling container adapted to receive and cool a suspension of crystal nuclei from the pump The apparatus may further include a stirrer, such as an anchor type impeller or a ribbon type impeller, or a scraper. The apparatus may further include a transfer line in fluid communication with the crystallizer and the pump.

Other aspects and features of the present invention will be further discussed in detail with reference to the following drawings and description.

DETAILED DESCRIPTION OF THE PREFERRED EMBODIMENT

Under the current state of the art in $\alpha$-APM crystallization processes, one must choose between either a method which does not require a long crystallization time, but which produces crystals of inferior physical properties, or a method which produces crystals of superior physical properties, but which requires a long crystallization time. A short crystallization time and crystals of superior physical properties are both desired attributes for a crystallization process, however. Therefore, a method for crystallizing $\alpha$-APM of good physical properties which does not require an unduly long crystallization time is desirable. The use of the novel method of the present invention achieves this by permitting the operation of an $\alpha$-APM crystallization process which does not require an unduly long crystallization time but which also avoids the uncontrolled spontaneous crystallization which leads to inferior physical properties of the crystals produced.

Figure 2:
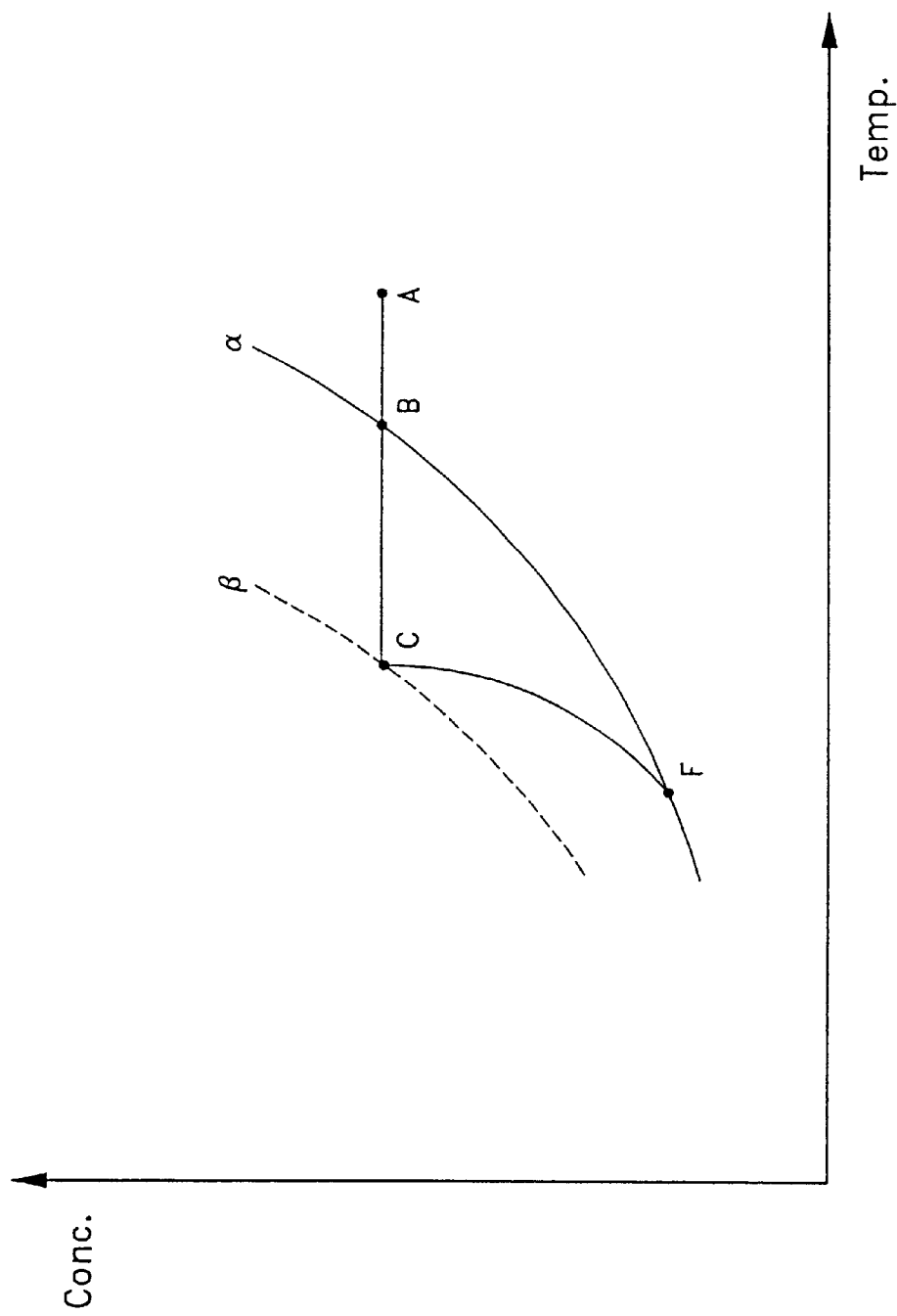
FIG. 2 illustrates a solubility-supersolubility diagram demonstrating the relationship between temperature and concentration of a solute in solution during cooling, in the absence of a solid phase.

The relationship between temperature and concentration of a solute in solution with regard to crystal formation is represented in FIG. 2. Curve $\alpha$ represents the solubility of $\alpha$-APM. Curve $\beta$, which runs approximately parallel with the solubility curve $\alpha$, is the boundary of the metastable region. Sometimes this curve is referred to as the curve of maximum permissible supersaturation or the limit of unstable supersaturation. The area between curves $\alpha$ and $\beta$ is defined as a metastable supersaturated region, in which spontaneous crystallization is improbable, but can occur if nucleation is initiated, or if seed crystals are introduced. The nucleation can be initiated by applying a form of energy to a solution in a metastable supersaturated solution.

In a conventional agitated crystallization process, mechanical stirring initiates the nucleation from a supersaturated $\alpha$-APM solution in the metastable supersaturated region. The nucleation caused by such mechanical stirring or agitation is substantial and extremely drastic, resulting in fine $\alpha$-APM crystals characterized as needlelike crystals. A likely explanation is that when an $\alpha$-APM metastable supersaturated solution is agitated, too many $\alpha$-APM nuclei are generated instantly and consume most of the solute that is over-dissolved with reference to the solubility level at a given temperature. As a result, the solution does not have much solute that can contribute to the growth of the small-sized nuclei at the temperature. The solution can be cooled to further precipitate the solute onto the existing crystals as seeds. However, since there are substantially too many fine crystals suspended in the solution, precipitation of the solute caused by the cooling cannot significantly grow the crystals and increase their sizes. Also, even if the mechanical stirring is slow or light, the generation of nuclei still occurs in a substantial and uncontrollable manner.

In order to avoid such drastic and substantial nucleation and to produce coarse crystals, a non-stirring crystallization of $\alpha$-APM was suggested. The non-stirring crystallization is conceptually described now in reference to FIG. 2. Consider, for example, a solution wherein the concentration and temperature are specified by point A. On gradually lowering the temperature, one arrives at point B on the solubility curve $\alpha$. If the system is free from solid phase, further lowering of the temperature does not lead to crystallization until point C is reached. At point C, the first crystals begin to appear, i.e., nucleate and grow, until the concentration diminishes to the equilibrium point of solubility given by point F. Further gradual cooling leads to movement along the equilibrium curve $\alpha$. Quicker cooling would correspond to displacement paths between the curves $\alpha$ and $\beta$. Rapid cooling, i.e., movement along curve $\beta$, would continuously produce new crystal nuclei. However, this non-stirring crystallization takes a very long time to produce coarse $\alpha$-APM crystals, as mentioned above.

Figure 3:
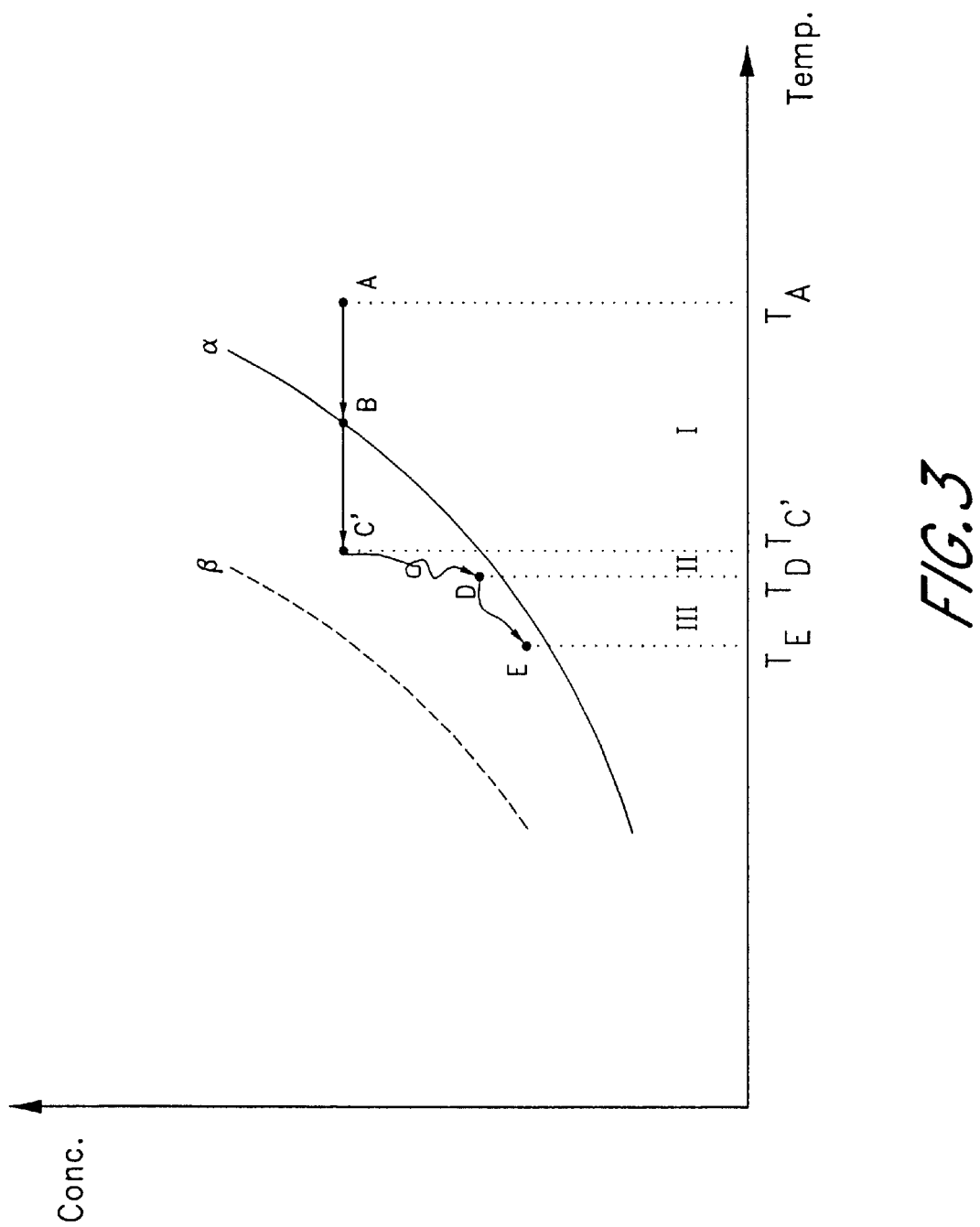
FIG. 3 illustrates a solubility-supersolubility diagram demonstrating the relationship between temperature and concentration of a solute in solution during the controlled crystallization process of the present invention.

The present invention provides a new concept for crystallization of a solute dissolved in a solution. Applying this concept to the crystallization of $\alpha$-APM, although not limited thereto, coarse $\alpha$-APM crystals are produced in a significantly shorter time on an industrial scale. FIG. 3 represents the principle of the controlled crystallization in accordance with the present invention. A solution at point A is prepared and cooled to a point C', representing a supersaturated solution in the metastable region. When the solution reaches point C', a certain form of mechanical energy is inputted to the solution, which initiates the nucleation in a controlled manner. The nucleation of $\alpha$-APM is controlled such that the rate of generation of nucleation is significantly reduced in comparison to that in the stirring crystallization. Only a part of the over-dissolved $\alpha$-APM at a given temperature is consumed and a constant number of $\alpha$-APM nuclei is generated in the nucleation, by which the solution moves from point C' to point D in FIG. 3. Then, $\alpha$-APM crystals spontaneously grow from these existing nuclei without significant additional nucleation, resulting in the change from point D to point E.

At a given temperature or concentration, a metastable solution becomes more stable as it gets closer to the solubility curve $\alpha$, and vice versa. In other words, a metastable solution close to the curve $\alpha$ is less likely to nucleate than another metastable solution close to the curve $\beta$ when the other conditions are the same. The controlled nucleation and following spontaneous crystal growth in the metastable region move the solution toward the solubility curve α, the solution gets stabilized. At the point E, the concentration of the solute is close to the solubility level and the solution is very stable.

The solution at point E still contains a considerable amount of solute. In order to produce coarser crystals and improve the yield of the crystallization, further crystallization proceeds. The α-APM slurry, the mixture of the solution and the crystals suspended therein, is cooled. As the temperature decreases, the solution at point E moves to the left toward the curve β within the metastable region. At a given temperature, some of the over-dissolved solute with reference to the solubility curve α can be precipitated. As the slurry becomes cooler, the existing crystals in the slurry continuously grow by consuming the over-dissolved α-APM solute. The cooling and continuous consumption of the solute lead to movement along the solubility curve α. New nucleation does not occur in an appreciable manner during the cooling since the solution is already in a stable state. As such, mechanical energy input such as agitation or stirring can be applied to the slurry without significant generation of additional nuclei.

Figure 1:
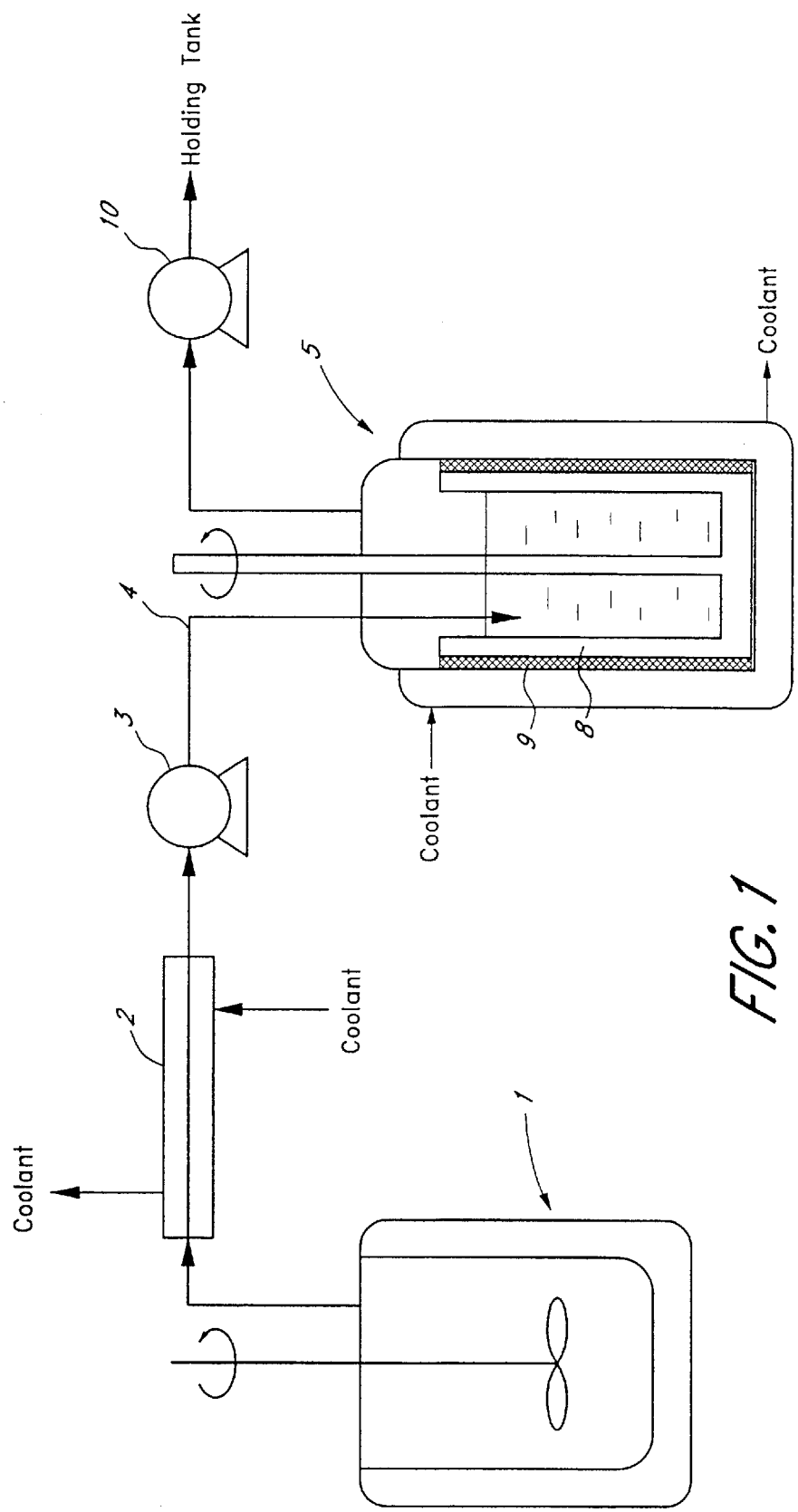
FIG. 1 illustrates a crystallization system of a preferred embodiment of the present invention.

Now referring to FIGS. 1 and 3, a preferred embodiment of the controlled crystallization in accordance with the present invention is described. A non-saturated aqueous α-APM solution is prepared by dissolving α-APM in water in a dissolver 1 as shown in FIG. 1 or as a result of the synthesis of α-APM. The solution is transferred to and cooled in a heat exchanger 2. The cooled metastable solution is fed to a nucleation pump 3, in which crystallization takes place initially through the formation of new nuclei. The nuclei then grow by consuming the solute in the metastable solution in a transfer line 4. The α-APM slurry is transferred to a crystallizer 5, in which further crystallization continues with coolant circulation and agitation.

The concentration and temperature of the solution is adjusted, for example in the dissolver 1. The concentration of the solution ranges from about 1.5 wt. % to about 7.0 wt. %, and the temperature in the concentration range is from about 35° C. to about 85° C. Preferably, the concentration of the solution is from about 3.0 wt. % to about 5.5 wt. % at a temperature ranged from about 55° C. to about 75° C., and more preferably the concentration is from about 3.5 wt. % to about 5.0 wt. % at from about 60° C. to about 70° C. The aqueous solution is represented by point A in FIG. 3.

As an example, an aqueous solution of about 4.0 wt. % α-APM at a temperature of about 65° C. is prepared. This solution is fed to the heat exchanger 2 positioned between the dissolver 1 and the nucleation pump 3 as shown in FIG. 1. Cooling proceeds with no change in α-APM concentration until a certain level of supersaturation (given by point C' in FIG. 3) in the metastable region is reached. During this cooling process (represented as Stage I in FIG. 3), no spontaneous nucleation takes place. This cooling is controlled such that the solution does not move too far left to hit the curve β of maximum permissible supersaturation, which will initiate the nucleation.

The relationship between the maximum allowable undercooling, $\Delta T_{max}$[° C.], and the cooling rate, $-dT/dt$ [° C./hr], for unseeded aqueous solutions of α-APM can be expressed as:

$$-dT/dt = 0.231*(\Delta T_{max})^{2.266}$$

The maximum allowable undercooling is the temperature difference between the curves α and β at a given concentration. This result can be used for the practical purpose of assessing the width of the metastable region for α-APM crystallization. In this embodiment of the present invention the heat exchanger 2 is designed such that the cooling is conducted less than the maximum allowable undercooling. The solution is cooled to a temperature in the range of from about 28° C. to about 80° C. with concentration from about 1.5 wt. % to about 7.0 wt. %. Preferably, the temperature after the heat exchange is from about 48° C. to about 66° C. at a concentration ranged from about 3.0 wt. % to about 5.5 wt. %., more preferably from about 51° C. to about 62° C. at a concentration from about 3.5 wt. % to about 5.0 wt. %. The coolant heat exchanging with the solution has a temperature ranged from about 0° C. to about 40° C. The coolant temperature is preferably from about 5° C. to about 30° C., more preferably from 10° C. to about 25° C.

Figure 4:
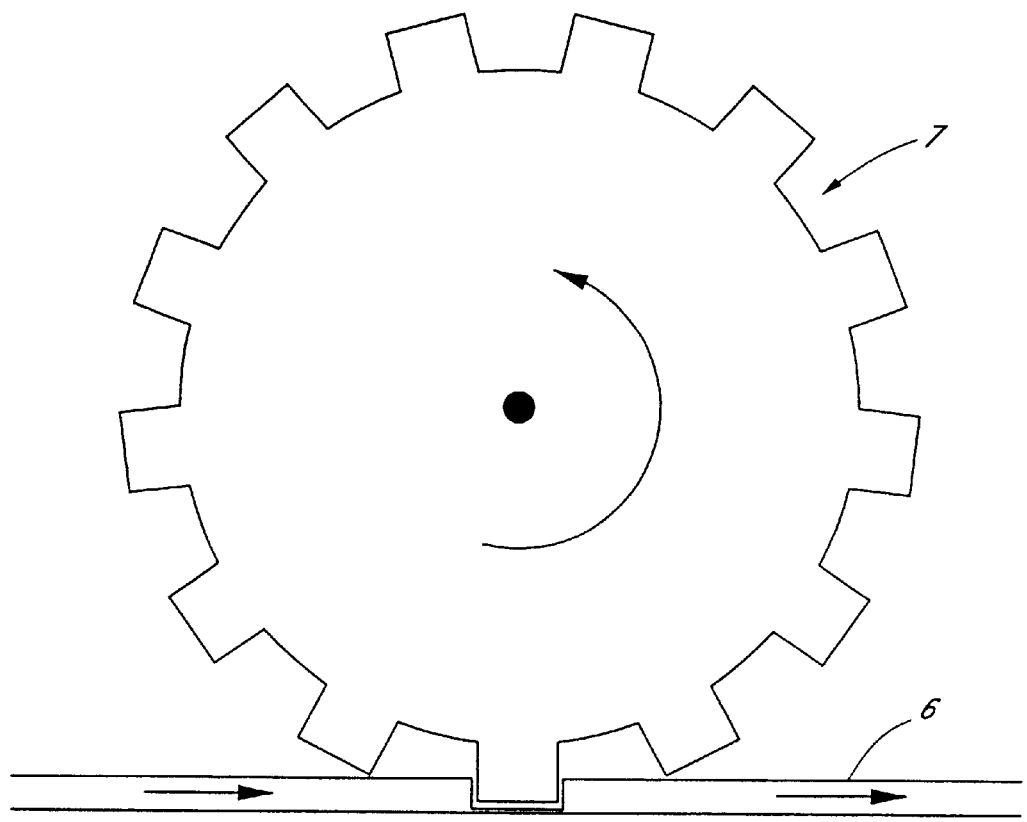
FIG. 4 illustrates conceptual operation of the nucleation pump of the preferred embodiment shown in FIG. 1.

The instant that the solution, at temperature $T_{C'}$ in a metastable state, enters the nucleation pump 3, the nucleation stage (designated as Stage II in FIG. 3) begins due to mechanical forcing from the rolling action of the nucleation pump 3. The pump 3 preferably includes a peristaltic pump, commonly referred to as a squeeze pump. FIG. 4 conceptually illustrates the peristaltic pump. In the pump, peristaltic flow is created in a tube 6 by a rotating roller mechanism 7 that alternately compresses and relaxes a section of the tubing 6. As the compressed section recovers its shape, suction is created, drawing in fluid which is then pushed forward by the next advancing roller. The pump action initiates nucleation and crystallization, thereby decreasing the concentration of α-APM in solution within the region of metastability. In this stage, concentration of the α-APM solution decreases rapidly (to point D of FIG. 3) as a result of consumption of the solute by both nucleation and crystal growth of the formed nuclei in the pump. While the peristaltic pump is used in the preferred embodiment of the present invention, any device or apparatus, which can generate a constant number of α-APM nuclei, can replace the pump.

When the solution containing crystals formed in the squeezed tubing part leaves the pump 3, substantially no further nucleation occurs and growth of the nuclei occurs in the upstream transfer line 4 of the crystallizer 5. The temperature in Stage II of FIG. 3 increases slightly due to the release of latent heat of crystallization, but cooling by heat exchange with the surrounding environment produces an overall reduction in the temperature of the mixture of crystals in solution. By the time the mixture of crystals in solution reaches the crystallizer 5, the concentration of solute is lowered close to the solubility level (point E in FIG. 3). Nucleation of α-APM ceases and a constant number of stable α-APM crystals are introduced into the crystallizer 5. The temperature of the mixture of crystals in solution upon introduction into the crystallizer 5 is from about 45° C. to about 60° C., although not limited thereto. Preferably, the temperature is in the range of from about 48° C. to about 55° C., more preferably 50° C. to 52° C., but higher temperatures may also be used.

While the slurry is entering into the crystallizer 5, the slurry's exposure to environmental air or atmosphere is preferably avoided. If the slurry contacts the air, it may trap and carry some of the gaseous phase into the slurry contained in the crystallizer 5, causing additional nucleation in the crystallizer 5 which generates fine nuclei. Substantial new formation of fine nuclei deteriorates the production of coarse α-APM crystals. Thus, in this preferred embodiment, the transfer line 4 is extended to the bottom of the crystallizer 5 at least at the time of charging the slurry into an empty crystallizer. Alternatively, the transfer line 4 can simply be extended below the top surface of the slurry if some of the slurry is contained in the crystallizer 5.

After the solution has undergone the controlled crystallization as described above, the mixture of α-APM crystals in solution is subjected to further crystallization by cooling the slurry and allowing the crystals in the feed solution to grow. Cooling in the crystallizer 5 takes place through the indirect heat exchange with a coolant circulating in an external cooling jacket, as shown in FIG. 1. The temperature of the coolant entering the cooling jacket is from about 0° C. to about 25° C. Preferably, it ranges from about 2° C. to about 20° C., more preferably from about 5° C. to about 15° C. Such cooling can be carried out with or without stirring of the slurry. Also the cooling crystallization can be carried out in either batch mode or continuous mode operation.

In the preferred embodiment of the present invention, the stirring of the slurry is used during the cooling without further substantial generation of nuclei. Any type of stirrers or mixers can be used to provide the stirring to the slurry in the crystallizer 5. Stirrers, however, may break up some of the crystals suspended in the solution by impact. Preferably, the stirrers, which either do not break the crystals or cause insignificant breakage of the crystals, are used. Exemplary stirrers include an anchor type impeller and, in the case of the industrial scale process, a ribbon type impeller. The crystallizer 5 shown in FIG. 1 has an anchor type impeller 8. A scraper 9 is preferably attached to the edges of the anchor or ribbon impeller 8 and keeps the interior walls of the crystallizer 5 free of adherent α-APM crystals by continuously scraping the crystallized deposit from the cold surface of the crystallizer wall. Alternatively, a separate scraper and stirrer may be used in the present invention. The rotational speed of the stirrer 8 can be determined depending on the size of the crystallizer and other parameters to effect significant mixing of the slurry contained in the crystallizer 5. However, the stirrer rotates at a speed of from about 2 rpm to about 100 rpm, preferably, the speed is from about 3 rpm to about 70 rpm, more preferably from about 5 rpm to about 50 rpm.

The stirring homogenizes the slurry of the α-APM crystals in the solution and enhances the heat transfer to the entire slurry. This significantly reduces the time required for this further precipitation by cooling of the α-APM solute dissolved in the solution. In conducting the crystallizing step, it is advantageous to minimize the amount of crystals adhering to the crystallizer wall. By minimizing crystal adherence to the walls, the heat transfer layer may be more extensively renewed. In sum, combined with a scraper renewing the heat transferring surface, the stirring of the slurry significantly enhances the heat transfer efficiency and allows the continuous operation of this further crystallization for an expanded period of time without stopping for removing scales.

If the process is to be conducted in a continuous mode, then in the initial stages of continuous mode operation when the mixture of crystals is first fed to the crystallizer 5, an optional aging step may be conducted. In the aging step, the initial charge of mixture of crystals in solution is allowed to "age" for a certain period of time without introduction of any additional solution into the crystallizer 5. After this initial aging period, the mixture of crystals in solution is introduced into the crystallizer 5 at the same rate that solution containing grown α-APM crystals is withdrawn from the crystallizer 5 and transferred to the receiving tank (not shown) by the action of a discharge pump 10. The mean residence time of mixture in the crystallizer 5 is in the range of from about 50 to 500 minutes, preferably 60 to 180 minutes, when operating in continuous mode. The temperature of the mixture during crystallization when operating in a continuous mode is in the range of from about 5° C. to about 45° C., preferably from 6° C. to about 35° C., more preferably from about 6° C. to 20° C.

The process may also be operated in batch mode. In batch mode, an amount of solution is introduced into the crystallizer 5 and allowed to cool without the addition or withdrawal of solution. After the crystallization step is completed, the solution is then withdrawn and transferred to the receiving tank (not shown). When operating in batch mode the temperature and residence time in the crystallizer 5 need not be as tightly controlled as when operating in continuous mode, thereby allowing greater flexibility in processing conditions.

After the crystallization discussed above, the α-APM slurry is subject to a solid-liquid separation. For instance, gravity filtration, pressure filtration, centrifuge filtration, reduced pressure filtration or evaporation of solvent can be used to separate the α-APM from its mother liquor. The solid-liquid separation is followed by a drying stage, which removes moisture retained in the separated solid α-APM. Normally, the solid α-APM is dried under elevated temperature.

By utilizing the crystallization method of the present invention, it is possible to obtain α-APM crystals with properties superior to those of crystals produced by conventional methods. The crystals demonstrate good filterability and solid-liquid separation. The crystals produced by the crystallization in accordance with the present invention are discrete and coarse crystals, needlelike in shape but thicker than those produced by the prior art cooling crystallization method wherein the solution is mixed. Also, the crystallization system apparatus is more compact than in conventional processes because of the remarkable reduction in the required residence time of the slurry. Thus, the present invention provides a method for α-APM crystallization that is markedly advantageous from economic viewpoint. The present invention is effective in batch mode as well as in continuous operation mode.

The following Examples illustrate the present invention in further detail. Those of skill in the art will recognize that there are numerous variations and modifications of this invention that are encompassed by its scope. Accordingly, the following Examples should only be considered illustrative of the present invention and not deemed to limit its scope. Some of the parentheses below are to correspond the devices and apparatuses used in the Examples to those shown in FIG. 1.

EXAMPLE I

An aqueous solution of α-APM entered the upstream transfer line (the transfer line between the dissolver 1 and the heat exchanger 2) to the crystallizer (the crystallizer 5). Tap water at a temperature ranging from about 7° C. to 8° C. was circulated through a cooling jacket (the heat exchanger 2) surrounding the transfer line. An aqueous solution of about 4 wt. % α-APM having a temperature of 65° C. was pulled through the transfer line into a pump (nucleation pump 3) at a rate of 20 ml/min. Crystals of α-APM began to form in the solution as it was forced through the nucleation, forming a slurry. The slurry (at a temperature of about 50° C. to 52° C.) was continuously fed to the crystallizer. The crystallizer had a volume of 3 liters and was equipped with a cooling jacket and anchor (anchor type impeller 8) with scraper (scraper 8). The impeller on the anchor was set to a rotation of 50 rpm. A coolant having a temperature of 5° C. was circulated through the cooling jacket of the crystallizer.

Once the crystallizer was entirely filled with slurry, charging of slurry to the crystallizer was stopped and the slurry was aged for 30 min to stabilize the crystallization system. After aging, charging of slurry to the crystallizer was reinitiated at a rate of 50 ml/min, and slurry was withdrawn from the crystallizer at the same rate, 50 m/min, so as to keep a constant volume of slurry in the crystallizer. The average residence time of slurry in the crystallizer was about 60 minutes, and the temperature of the slurry during crystallization under steady state conditions was in the range of 6° C. to 12° C. The crystallization process was carried out for two consecutive days, during which time scale was never generated on the sides of the crystallizer. The slurry thus produced demonstrated excellent filterability, i.e., the water content of the resulting wet crystals of α-APM ranged from 37 to 45 wt. %.

EXAMPLE II

An industrial scale crystallization system as illustrated in FIG. 1 was set up. The dissolver 1 corresponds to a tank for containing an aqueous α-APM solution, which was neutralized from α-APM·HCl in a final stage of the α-APM synthesis. The concentration of the α-APM solution was adjusted to 4.8–5.0 wt. % at the temperature of 68° C. The supersaturated α-APM solution was fed through the heat exchanger 2 by the action of the peristaltic pump 3 at a rate of 25.8 L/min. A coolant at a temperature between 20–28° C. circulated through a cooling jacket of the heat exchanger 2. The α-APM solution was cooled to a temperature of 56–58° C. by indirect heat-exchange with the coolant. The peristaltic pump 3 initiated the generation of α-APM nuclei, forming a slurry, which is a mixture of the nuclei and supersaturated solution. In the transfer line 4 to the crystallizer 5, the crystals grew from the nuclei. The temperature of the slurry before entering the crystallizer 5 was 54–56° C.

The crystallizer 5 is in a cylindrical shape with a diameter of about 2.3 m and a height of 3 m, and the internal volume is about 12 KL. The interior surface of the crystallizer 5 is made of stainless steel and surrounded with a cooling jacket. A coolant at a temperature of 4.5–5.0° C. continuously circulated in the cooling jacket. In this industrial scale crystallizer 5, a ribbon type impeller was installed. This impeller continuously rotated at about 11 rpm to mix the slurry contained in the crystallizer 5. Attached to the impeller was a scraper, the distal edge of which moves at a linear speed of about 79.5 m/min. The transfer line 4 was extended below the top surface of the slurry in the crystallizer 5 to prevent the slurry contacting the atmosphere. After 8–10 KL of the slurry was charged in the crystallizer 5, a continuous mode operation started by withdrawing the slurry at the same rate as it was being introduced thereto. The average residence time of slurry in the crystallizer 5 was about 390 min, and the temperature of the slurry under steady state conditions was in the range of 12–17° C. The water content of the resulting wet crystals of α-APM ranged from 39 to 42 wt. %.

Although this invention has been described in terms of a certain preferred embodiment, other embodiments will become apparent to those of ordinary skill in the art, in view of the disclosure herein. Accordingly, the present invention is not intended to be limited by the recitation of preferred embodiments, but is instead intended to be defined solely by reference to claims that follow.

What is claimed is:

1. A method of producing crystals of α-L-aspartyl-L-phenylalanine methyl ester ("α-APM"), comprising:
   forming a supersaturated solution of α-APM;
   providing the supersaturated solution to a nucleating apparatus, which is a peristaltic pump;
   initiating nucleation of α-APM crystal nuclei at the nucleating apparatus, thereby forming a suspension of crystal nuclei in the supersaturated solution; and
   growing the α-APM crystal nuclei in the supersaturated solution from the nucleating apparatus, wherein the supersaturated solution from the nucleating apparatus does not return to the nucleating apparatus.

2. The method of claim 1, wherein the formation of the supersaturated solution comprises:
   preparing a non-supersaturated α-APM solution; and
   cooling the non-supersaturated solution to form the supersaturated solution.

3. The method of claim 2, wherein the concentration of the non-supersaturated α-APM solution is in the range from about 1.5 wt. % to about 7.0 wt. %.

4. The method of claim 3, wherein the concentration of the non-supersaturated solution is from about 3.0 wt. % to about 5.5 wt. %.

5. The method of claim 2, wherein the temperature of the non-supersaturated α-APM solution is in the range from about 35° C. to about 85° C. before cooling.

6. The method of claim 5, wherein the temperature of the non-supersaturated α-APM solution is from about 55° C. to about 75° C. before cooling.

7. The method of claim 2, wherein the cooling is conducted at less than a maximum allowable undercooling at a concentration.

8. The method of claim 2, wherein the cooling is conducted by heat exchanging with a coolant.

9. The method of claim 1, wherein the solution is an aqueous solution.

10. The method of claim 9, wherein the concentration of α-APM in the supersaturated solution prior to initiating nucleation is greater than about 3.5 wt. %.

11. The method of claim 1, wherein the initiating nucleation at the nucleating apparatus is conducted by mechanical forcing on the solution.

12. The method of claim 1, wherein the peristaltic pump applies compressive force to the supersaturated solution and releases the force therefrom, thereby generating crystal nuclei.

13. The method of claim 12, wherein the supersaturated solution subject to the compressive force of the peristaltic pump is substantially free of crystals or crystal nuclei.

14. The method of claim 1, wherein the initiating nucleation at the nucleating apparatus comprises introducing seed crystals into the solution.

15. The method of claim 1, wherein the initiating nucleation is conducted at a solution temperature ranging from about 28° C. to about 80° C.

16. The method of claim 15, wherein the solution temperature is from about 48° C. to about 66° C.

17. The method of claim 1, wherein the growing the α-APM crystal nuclei comprises a spontaneous growing stage after the initiation of nucleation and a forced growing stage after the spontaneous growing stage.

18. The method of claim 17, wherein the spontaneous growing stage proceeds at a supersaturated solution temperature ranging from about 45° C. to about 60° C.

19. The method of claim 17, wherein the forced growing stage comprises cooling the suspension of crystal nuclei in the supersaturated solution.

20. The method of claim 19, wherein the cooling is conducted at a solution temperature ranging from about 5° C. to about 60° C.

21. The method of claim 19, wherein the cooling is conducted in a batch mode operation.

22. The method of claim 19, wherein the cooling is conducted in a continuous mode operation.

23. The method of claim 19, wherein the cooling is conducted for a time of from about 50 to about 500 min.

24. The method of claim 19, wherein the suspension of crystal nuclei in the supersaturated solution is stirred during the cooling.

25. The method of claim 24, wherein the stirring is conducted by an anchor type impeller or a ribbon type impeller.

26. The method of claim 25, wherein a scraper is attached to the impeller.

27. The method of claim 25, wherein the stirring is conducted at from about 2 rpm to about 100 rpm.

28. The method of claim 19, wherein the suspension of crystal nuclei in the supersaturated solution is not in contact with a gaseous atmosphere before the cooling.

29. The method of claim 1, further comprising conducting a solid-liquid separation after growing the α-APM crystal nuclei in the supersaturated solution to form α-APM crystals.

30. The method of claim 29, further comprising drying the α-APM crystals under elevated temperature.

31. The method of claim 1, wherein the method is performed in an industrial scale.

32. The method of claim 31, wherein the growing of α-APM crystal comprises cooling the suspension of crystal nuclei in the supersaturated solution in a container having a capacity greater than 1 KL.

33. A method of continuously crystallizing a solute dissolved in a solvent, comprising:
continuously feeding a supersaturated solution to a peristaltic pump;
continuously generating crystal nuclei of a solute in the supersaturated solution at the pump by rolling action of the pump to form a suspension of crystal nuclei in the supersaturated solution;
continuously transferring the suspension to a crystallizer; and
continuously growing the crystal nuclei by cooling the suspension in the crystallizer;
wherein crystal nuclei or grown crystals are not fed to the peristaltic pump throughout the crystallization.

34. The method of claim 33, wherein the continuous feeding comprises continuously cooling a non-saturated solution to form a supersaturated solution.

35. The method of claim 33, wherein the continuous growing comprises continuously stirring the suspension.

36. The method of claim 35, wherein the stirring is provided by an anchor type impeller or a ribbon type impeller.

37. The method of claim 33, wherein the continuous growing comprises continuously scraping an internal surface of the crystallizer.

38. The method of claim 33, further comprising continuously withdrawing the suspension from the crystallizer.

39. The method of claim 33, wherein the method is performed in an industrial scale.

40. The method of claim 39, wherein the crystallizer has a capacity greater than 1 KL.

41. The method of claim 33, wherein the peristaltic pump comprises:
a flexible tube configured to pass the supersaturated solution therethrough; and
a mechanism configured to alternately compress and release a portion of the tube.

42. A method of crystallizing a solute, comprising:
preparing a supersaturated solution of a solute dissolved in a solvent;
creating a flow of the supersaturated solution in a direction by feeding the supersaturated solution through a flexible tube;
applying compressive force to the supersaturated solution at a point in the flow and releasing the force therefrom, wherein the application and release of the compressive force comprises alternately compressing and releasing a portion of the tube, thereby generating crystal nuclei of the solute in the supersaturated solution while maintaining the solution supersaturated, wherein the supersaturated solution subject to the compressive force is substantially free of crystals or crystal nuclei, and wherein the generated crystal nuclei are suspended in the supersaturated solution; and thereafter
growing the crystal nuclei suspended in the supersaturated solution.

43. The method of claim 42, wherein the preparing the supersaturated solution comprises adjusting concentration of the solution.

44. The method of claim 42, wherein the applying and releasing compressive force is performed continuously.

45. The method of claim 42, wherein the growing the crystal nuclei comprises cooling the crystal nuclei and the supersaturated solution.

46. The method of claim 44, wherein the cooling comprises containing the crystal nuclei and the supersaturated solution in a temperature controlled container.

47. The method of claim 46, wherein the temperature controlled container comprises a cooling jacket configured to circulate a coolant therethough.

48. The method of claim 42, wherein the growing the crystal nuclei comprises stirring of the crystal nuclei and the supersaturated solution.

49. The method of claim 42, wherein the method is performed in an industrial scale.

50. The method of claim 42, wherein the method is performed continuously.

51. The method of claim 42, wherein the solute is α-L-aspartyl-L-phenylalanine methyl ester.

52. The method of claim 42, wherein the solvent is an aqueous solvent.

53. The method of producing a chemical compound, comprising the crystallizing method of claim 42, wherein the chemical compound comprises the solute.

54. The method of claim 53, wherein the chemical compound comprises α-L-aspartyl-L-phenylalanine methyl ester.

55. The method of claim 53, further comprising performing solid-liquid separation after the growing.

56. The method of claim 55, further comprising drying the solid separated in the solid-liquid separation.

57. The method of claim 33, wherein the continuous growing is performed without substantial formation of new nuclei.

58. The method of claim 1, wherein the growth of crystal nuclei is carried out without substantial formation of new crystal nuclei.

59. The method of claim 1, wherein the growing crystal nuclei is carried out in a vessel having an internal surface contacting the suspension, and wherein the growing further comprises renewing at least a partial area of the surface.

60. The method of claim 59, wherein the renewing comprises scraping the at least partial area of the surface.

61. The method of claim 42, wherein the growing crystal nuclei is carried out in a vessel having an internal surface contacting the suspension, and wherein the growing further comprises clearing crystals deposited on the surface.

62. A method of crystallization of α-L-aspartyl-L-phenylalanine methyl ester ("α-APM"), comprising:
providing a crystallizing vessel comprising an inner surface;
supplying a solution of α-APM to the crystallizing vessel such that the solution contacts the inner surface, wherein the supply of the solution comprises nucleating α-APM crystal nuclei at a peristaltic pump, thereby forming a suspension of crystal nuclei in the solution;
cooling at least part of the surface, thereby cooling the solution;
stirring the solution in the crystallizing vessel; and
renewing at least a partial area of the inner surface.

63. The method of claim 62, wherein the renewing comprises scraping the at least partial area of the inner surface.

64. The method of claim 62, wherein the stirring comprising continuously rotating a stirrer within the crystallizing vessel.

65. The method of claim 64, wherein the stirrer comprises a blade and a scraper attached to the blade, wherein the scraper is configured to contact the at least partial area of the inner surface.

66. The method of claim 65, wherein the scraper scrapes the at least partial area of the inner surface as the stirrer rotates.

67. The method of claim 62, wherein the solution is provided to the crystallizer along with solid particles suspended therein.

68. The method of claim 62, wherein the solution supplied to the crystallizing vessel is a supersaturated solution of α-APM.

69. The method of claim 62, wherein the renewal of the surface takes place while stirring.

70. The method of claim 62, wherein the renewal comprises removing particles of α-APM deposited on the inner surface.

71. The method of claim 62, wherein the nucleation comprises applying compressive force to the solution and releasing the force, thereby generating the α-APM crystal nuclei, wherein the solution subject to the compressive force is substantially free of crystals or crystal nuclei, and wherein the generated crystal nuclei are suspended in the solution.

72. The method of claim 33, wherein the solute is α-L-aspartyl-L-phenylalanine methyl ester.

* * * * *